United States Patent [19]

Cook et al.

[11] 4,005,102

[45] * Jan. 25, 1977

[54] PROCESS FOR MAKING 4-NITRO-N-METHYLPHTHALIMIDE

[75] Inventors: Newell C. Cook, Schenectady; Gary C. Davis, Albany, both of N.Y.

[73] Assignee: General Electric Company, Schenectady, N.Y.

[ * ] Notice: The portion of the term of this patent subsequent to June 24, 1992, has been disclaimed.

[22] Filed: Aug. 18, 1975

[21] Appl. No.: 605,397

Related U.S. Application Data

[62] Division of Ser. No. 486,356, July 8, 1974.

[52] U.S. Cl. .................. 260/326 N; 260/346.3; 260/515 R; 260/591; 260/612 R; 260/645; 260/646

[51] Int. Cl.² ...................................... C07D 209/34

[58] Field of Search .............................. 260/326 N

[56] References Cited

UNITED STATES PATENTS

| | | | |
|---|---|---|---|
| 2,826,611 | 3/1958 | Fischback et al. | 260/688 |
| 3,100,797 | 8/1963 | Harris et al. | 260/688 |
| 3,925,426 | 12/1975 | Vogel | 260/369 |
| 3,933,852 | 1/1976 | Cook et al. | 260/326 N |

OTHER PUBLICATIONS

Ponomarenko, "Chem. Abstracts," vol. 44, p. 7810b (1950) (original article unavailable).
Groggins, "Unit Processes in Organic Synthesis," 3rd edition, pp. 1 and 10 (1947).

Primary Examiner—Dolph H. Torrence
Attorney, Agent, or Firm—Joseph T. Cohen; Jerome C. Squillaro

[57] ABSTRACT

Nitrated derivatives of aromatic compounds are obtained by contacting the latter, in the presence of methylene chloride as a reaction medium, with concentrated nitric acid in the presence of concentrated sulfuric acid, and thereafter isolating the formed nitro derivatives.

1 Claim, No Drawings

PROCESS FOR MAKING 4-NITRO-N-METHYLPHTHALIMIDE

This is a division, of application Ser. No. 486,356, filed July 8, 1974.

This invention is concerned with a process for making nitrated derivatives of aromatic compounds. More particularly, the invention is concerned with a process for making nitrated aromatic compounds containing from 6 to 18 carbon atoms, which process comprises contacting the aromatic compound, in the presence of methylene chloride as a reaction medium, with from 80 to 100% concentration sulfuric acid and 90 to 100% concentration nitric acid, advantageously within a temperature range of from about −20° to 50° C., or even somewhat higher, and thereafter isolating the nitro compound, e.g., by extraction with additional methylene chloride.

Dinitrobenzenes and dinitrotoluenes (as well as other dinitro aromatic hydrocarbons) are important intermediates in the preparation of diamino derivatives thereof which are obtained by the reduction with hydrogen of the corresponding dinitro compound. These diamino compounds, for instance, m-phenylenediamine, p-phenylenediamine, and toluene diisocyanate (which is made from dinitrotoluene) are important ingredients in the preparation of commercial resinous compositions. For instance, diaminobenzenes can be reacted with 2,2-bis[4-(3,4-dicarboxyphenoxy)phenyl] propane dianhydride to give polymers having good high temperature properties. Polyetherimide polymers derived in the above manner are more particularly disclosed and claimed in U.S. Patent 3,787,475, issued Jan. 23, 1974, and assigned to the same assignee as the present invention.

Toluene diisocyanates are used in making resinous products by reacting the latter with polyols in the manner disclosed in U.S. Pat. Nos. 3,781,229 and 3,781,235, both issued Dec. 25, 1973, and in U.S. Pat. No. 3,801,687 issued Apr. 2, 1974. Such resinous products can be converted to foams having utility as insulation in refrigerators, and can also be employed as wire enamels for conductors used in motor windings.

In the past, these dinitrohydrocarbons have been prepared in large quantities by fairly well-known techniques. However, it has become desirable not only to improve the yields of these dinitrobenzene compounds but also to reduce the hazards and the cost thereof by virtue of more simplified processing techniques. Unexpectedly, we have discovered that aromatic compounds, e.g., aromatic hydrocarbons, can be readily nitrated and the nitrated products can usually be obtained in almost quantitative yields, to give mainly the dinitro derivatives in almost reaction grade purity. In accordance with our invention, the aromatic compound dissolved in $CH_2Cl_2$ as a reaction medium, is contacted with concentrated nitric acid in the presence of concentrated sulfuric acid to form the nitro derivatives thereof. Thereafter, the nitro derivatives are isolated from the reaction mixture, advantageously using additional methylene chloride for extraction purposes. The methylene chloride can be readily evaporated from the nitrated compound to leave behind the essentially pure nitrated derivative and to yield unchanged methylene chloride which can be recycled for further solvent and extraction purposes. By these techniques, we are able to form nitro derivatives, particularly dinitro compounds, on a continuous basis rather than the batch operation which has formerly been used extensively in making dinitro compounds.

The use of the methylene chloride as the solvent in the treatment of the aromatic hydrocarbon with the nitric acid in the sulfuric acid medium is important for a number of reasons. Methylene chloride is completely stable in nitric acid in all concentrations up to its boiling point of 40° C. or somewhat higher, and was alone in being able to resist degradation or resist conversion to other products as compared to other halogenated derivatives such as chloroform and methyl chloroform. Moreover, the aforesaid halogenated derivatives, other than methylene chloride, did not have the desired volatility and solubility affinity for the reaction mixture and the nitrated products therefrom to insure efficient and rapid removal of the desired nitrocompounds. Also, it was found that only methylene chloride was able to maintain its integrity sufficiently in a strongly acidic environment.

It was also found that in a number of instances, by using the methylene chloride, a limiting temperature in the neighborhood of around 42° C. could be attained, thus eliminating local hot spots and sudden temperature rises and automatically restricting the nitration of the aromatic compound to the mono or dinitro derivative and thus avoiding the formation of trinitro derivatives (which can be explosive in nature). Furthermore, the methylene chloride avoided the need for any extra care which might be required to insure that excess nitric acid was not present to cause the formation of dangerous trinitro derivatives.

The methylene chloride is completely miscible in nitric acid above 90% concentration thus facilitating reaction when nitrations are slow; the methylene chloride, however, is immiscible with nitric acid below 80% concentration, thus diminishing side reactions when highly reactive compounds are being nitrated.

It was also found that some of the nitrated products were solid and, previously, difficulty was encountered in avoiding separation of the nitrated compounds during the nitration reaction. The use of the methylene chloride, because it was such a good solvent for the nitrated compounds (as well as being a good solvent for unnitrated products), avoided this bothersome separation.

The aromatic compounds which can be nitrated in accordance with our process can be any aromatic monocyclic or polycyclic (or fused) ring compound which has at least one nuclearly-bonded hydrogen capable of being replaced by an $NO_2$ group and which is free of any substitution which will significantly and undesirably affect the ability of the nitration reaction to proceed. Thus, these aromatic compounds may be strictly hydrocarbon compounds, or they may contain functional or side groups, such as, ethers, carbonyls, carboxyls, halogens, anhydrides, nitriles, aliphatic or alicyclic groups, aromatic compounds containing heterocyclic groups attached thereto, etc.

Among such aromatic compounds which advantageously can be employed in the practice of the present invention may be mentioned, for instance, aromatic monocyclic and polycyclic hydrocarbon compounds, e.g., benzene, toluene, xylene, mesitylene, biphenyl, naphthalene, anthracene, diphenyl methane, diphenyl ethane, etc.; halogenated derivatives of such aromatic monocyclic and polycyclic hydrocarbons, for example, chlorobenzene, dichlorobenzene, dibromobenzene, chloromesitylene, dichlorotoluene, various halogenated biphenyl derivatives, the various halogenated naphthalene derivatives, the various halogenated anthracene derivatives, etc.; aromatic ethers e.g., diphenyl oxide, halogenated derivatives of such phenyl ethers, for example, and mono- and dichlorodiphenyl oxide, etc.; aliphatic substituted diphenyl ethers, particularly those containing from 1 to 3 carbon atoms in the aliphatic nucleus, for example, the mono- to tetramethyldiphenyl oxide (including its various isomers), diethyl substituted diphenyl oxide (and its various isomers), etc.; benzophenone and the various substituted products thereof, for instance, the mono- to tetramethyl-substituted dibenzophenone and the various halogenated substituted dibenzophenones, for instance, 3,3'-dichlorobenzophenone, etc.; other aromatic compounds such as benzoic acid, phthalic anhydride, chlorophthalic anhydride, the various phthalimides such as phthalimide itself, N-methylphthalimide, N-ethylphthalimide, etc. and halogenated derivatives of such phthalimides, for instance, monochloro N-methylphthalimide (including the various isomers), etc.

It will be evident that intended within the scope of this invention are both mono-nitrated and dinitrated products where there is a maximum of two nitro groups in the aromatic compound nucleus. Where there is more than one cyclic aromatic nucleus in the aromatic compound, there is correspondingly only one nitro group per aromatic ring.

The amount of methylene chloride used as a solvent in the nitration step is not critical. Generally, however, we have found that for each part by weight of the aromatic compound, from about 1 to 50 parts or more of the methylene chloride are advantageously employed. Since the methylene chloride is also used as an extractant after the reaction is completed, the methylene chloride amount initially employed for solvent purposes can be minimal and later the extra amount of methylene chloride is added for the extraction step. Generally, the minimum amount of methylene chloride used should be sufficient to limit the reaction temperature to no higher than about 42°–45° C. at atmospheric pressure. Also the amount of methylene chloride used should be sufficient to permit essentially complete solution of the aromatic compound in the methylene chloride and to prevent undesirable separation of the nitrated product before complete nitration is accomplished.

When employing the methylene chloride for extraction purposes, we have found that, on a weight basis for each part of nitrated product, one can advantageously employ from about 0.5 to 8 parts or more of additional methylene chloride for the extraction function. In all instances when carrying out the nitration reaction stirring of the reaction mixture should be carried out for more intimate contact of the reactants; a similar degree of stirring should be resorted to when employing the methylene chloride for extraction purposes.

The sulfuric acid solvent initially employed should be within 80 to 100% $H_2SO_4$. If lower concentrations of $H_2SO_4$ are employed initially, the amount of water liberated from the nitration reaction (with the nitric acid) will undesirably dilute the sulfuric acid thus causing a problem because of the decreased solubility of the nitrated products in the reaction mixture, particularly the water which is formed as a result of the reaction with the nitric acid. This might cause a separation problem during the step of extraction with the methylene chloride.

The concentration of nitric acid must also be within about 90 to 100% concentration in order to minimize the amount of water formed so as not to unduly dilute the sulfuric acid. The amount of nitric acid used should be relatively close to the stoichiometric amount required to attach the desired number of nitro groups on the aromatic nucleus or nuclei. As pointed out above, however, any substantial excess of nitric acid is not critical because the $CH_2Cl_2$ solvent will limit the degree of nitration thereby avoiding hazardous situations and possible explosive compositions.

In carrying out the reaction, one method comprises dissolving the aromatic hydrocarbon in the methylene chloride and placing the solution in a reactor equipped with a stirrer and means for heating or cooling the reactor. After heating the solution to the desired temperature (usually reflux temperature of about 40°–45° C.), a mixture of concentrated nitric acid and concentrated sulfuric acid is added slowly over a period of time advantageously ranging from about 15 minutes to about one to two hours or more. After stirring the mixture for a period of time ranging from about 30 minutes to about 2 to 3 hours at the reflux temperature, the mixture is cooled to room temperature at which time two distinct layers are usually visible. The upper methylene chloride layer is separated and the bottom acid layer is extracted with additional methylene chloride, preferably in several fractional extractions. The extracts and the top methylene chloride layers are sent through a silica gel (or other appropriate means) to remove residual acid, the methylene chloride removed by evaporation to give the nitrated product.

The continuous extraction of the bottom acid solution with methylene chloride is advantageously carried out in a closed loop reactor resembling a Dean Stark apparatus and consisting of an extraction column equipped with a stirrer into which the reaction product is introduced. Methylene chloride (extractant) is introduced continuously into the bottom of the extraction column. At the upper end of the extraction column is an arm through which the overflow of the extractant and reaction product (separated from $H_2SO_4$) is carried into a reservoir equipped with a heater operable within a range of about room temperature to 100° C. whose function is to evaporate the methylene chloride and concentrate the nitrated aromatic compound. The methylene chloride vapor is condensed and recycled by gravity to the bottom of the extraction column and continues recycling until extraction is complete. At this point, all the nitrated product is in the methylene chloride contained in the reservoir.

As pointed out previously, one of the advantages of using methylene chloride as a solvent during the nitration reaction is that lower temperatures can be used and there is practically no danger of excessive nitration to form compounds having more than two nitro groups per aromatic ring thereon which could present a hazardous condition. Generally the temperature at which the nitration is carried out is sufficiently productive within the range of from about 50° to 45° C. However, lower temperatures can be employed beginning with about −20° to −10° C. up to the reflux temperature of the mixture (or even higher especially when superatmospheric pressures are used).

During the entire nitration reaction, it is desirable that an inert atmosphere, for instance, a blanket of nitrogen be employed. Generally, atmospheric pressures are adequate for maintaining the reaction but it will of course be apparent to those skilled in the art that subatmospheric or even superatmospheric conditions may be employed without departing from the scope of the invention. Vigorous stirring is employed throughout the reaction period.

As a result of carrying out the reaction where dinitro derivatives are intended, it has been found that for the most part a mixture of dinitrated isomers is obtained in which there is a fairly constant ratio of the ortho, para, and meta isomers. This seems to be the case whether a mononuclear hydrocarbon or a dinuclear hydrocabon aromatic compound is being subjected to nitration. When a mononuclear compound is being nitrated such as benzene and toluene, generally about 70 to 80% is the meta-dinitro isomer. The yields of dinitrated products are exceptionally good and in some instances are quantitative.

In order that those skilled in the art may better understand how the present invention may be practiced, the following examples are given by way of illustration and not by way of limitation.

Unless stated otherwise, the extracted nitrated product combined with the methylene chloride was passed through a column of silica gel to remove traces of sulfuric acid; the removal of methylene chloride was accomplished under vacuum in a rotary film evaporator.

EXAMPLE 1

7.8 grams (0.1 mol) benzene was placed in the above-described nitration vessel together with 40 cc. of methylene chloride. While stirring the mixture, it was brought up to reflux temperature by gentle heating (about 42° to 45° C.). At this point a mixed acid consisting of 30 cc. of 95.5% $H_2SO_4$ and 9.5 cc. (0.22 mol) of 98.1% $HNO_3$ was added dropwise to the stirred solution over a period of approximately 25 minutes. The reaction mixture was then maintained at the reflux temperature of the mass for an additional 90 minutes and then cooled to room temperature, at which point the mixture separated into two layers, a top methylene chloride layer and a bottom acid layer. These layers were separated and the acid layer was extracted twice with additional 40 cc. portions of methylene chloride. The extracts and methylene chloride layer were then placed through a column of silica gel, the methylene chloride removed to give a quantitative yield of pure, mixed ortho, para, and meta dinitrobenzenes in the isomer ratios of about 85% of the meta-isomer, 13% of the ortho-isomer, and 2% of the para-isomer.

EXAMPLE 2

Employing the same equipment as described in Example 1, 9.2 grams (0.1 mol) toluene was formed into a solution with 40 cc methylene chloride. The solution was brought to reflux temperature (about 42° C.) and at this point, a mixed acid consisting of 25 cc. of 95.5% $H_2SO_4$ and 9.5 cc. (0.22 mol) 98.1% $HNO_3$ was added dropwise over a period of approximately 20 minutes. The mixture was stirred at the reflux temperature of the mass for an additional 90 minutes and then cooled to room temperature to yield two distinct layers, a top methylene chloride layer and a bottom acid layer. The latter layer was extracted twice with 40 cc. portions of methylene chloride and the extracts and the methylene chloride layer were treated with silica gel, and methylene chloride solvent removed to give a quantitative yield of pure mixed dinitrotoluenes in a weight ratio of about 78% of the 2,4-isomer, 19% of the 2,6-isomer, and 3% of other isomers.

EXAMPLE 3

In this example, 17 grams (0.1 mol) diphenyl ether was added to the aforesaid reaction vessel used in the preceding examples along with 40 cc. methylene chloride. An acid mixture consisting of 30 cc. of 85% $H_2SO_4$ and 8.6 cc. (0.2 mol) of 98.1% $HNO_3$ was added dropwise over a period of 75 minutes to the vigorously stirred solution a diphenyl ether and held at a temperature from about 5° to 10° C. throughout the addition. The reaction mixture was then stirred at 15° C. for an additional 180 minutes and then heated to 25° C. and stirred at this temperature for an additional 15 hours. The reaction mixture was extracted twice with methylene chloride (a 250cc. portion followed by a 100 cc. portion). The extracts were treated with silica gel and the solvent was removed to give 25.99 grams of recovered material consisting of about 90% of mixed dinitrodiphenylethers. Analysis of the product indicated that there was one nitro group on each phenyl nucleus.

EXAMPLE 4

In this example, a number of other aromatic compounds were nitrated using the procedures described in Examples 1 to 3. The following Table I shows the result of such tests whereby two nitro groups were introduced into the aromatic compound to form a dinitrated product. Where there was a single aromatic nucleus, two nitro groups formed on the single nucleus. Where, however, the aromatic compound consisted of two aromatic nuclei, one nitro group was introduced into each aromatic nucleus. All nitrations used 0.1 mol of aromatic compound except for the diphenyl sulfone which used 0.025 mol. Two equivalents of nitric acid (98.3% concentration) were used in each case except for the monochlorobenzene which used a 5% excess of nitric acid. All the nitrated materials were readily extracted from the sulfuric acid with methylene chloride except for the dinitrodiphenyl sulfone which was slower. In each instance, from 30 to 50 cc. of methylene chloride was used as the solvent medium during the nitration reaction. The first time tabulated under the heading "Time" is for the addition of the nitric-sulfuric acid mixture, and the following times denote reaction periods at the temperatures indicated. Very little, if any, mononitrated product was obtained and such product generally ranged from about 0 to about 3%, by weight, of the total product.

TABLE I

| Compound | $H_2SO_4$ cc | % Concent. | Temp. (° C) | Time (hr) | Total Weight Reaction Product (grams) | % Yield Dinitrated Product |
|---|---|---|---|---|---|---|
| o-Xylene | 25 | 95.6 | 5 | 1.0 | 18.91 | 96.4 |
|  |  |  | 25 | 2.0 |  |  |
| Chlorobenzene | 30 | 95.6 | 41 | 0.5 | 19.63 | 96.9 |
|  |  |  |  | 4.0 |  |  |
| Naphthalene | 30 | 85 | 10–15 | 1.0 | 19.44 | 89.1 |
|  |  |  | 15 | 2.0 |  |  |
| Diphenyl | 20 | 95.5 | 10–15 | C.5 | 23.97 | 94.7 |
|  |  |  | 25 | 1.0 |  |  |
| Diphenylmethane | 20 | 95.5 | 5–15 | 0.5 | 25.21 | 93.6 |
|  |  |  | 41 | 3.5 |  |  |
| Dibenzyl | 20 | 95.5 | 5–15 | 0.5 | 27.00 | 94.0 |
|  |  |  | 25 | 1.0 |  |  |
| Benzophenene | 20 | 95.5 | 10–30 | 0.5 | 26.78 | 92.8 |
|  |  |  | 30 | 1.5 |  |  |

TABLE I-continued

| Compound | H₂SO₄ cc | % Concent. | Temp. (°C) | Time (hr) | Products Total Weight Reaction Product (grams) | % Yield Dinitrated Product |
|---|---|---|---|---|---|---|
| Diphenyl-sulfone | 10 | 100 | 41 5.0 | 0.5 | 6.27 | 81.3 |

EXAMPLE 5

10.6 grams (0.1 mol) o-xylene was dissolved in 40 cc. methylene chloride and to this was added a mixture consisting of 12.5 cc. of 80% $H_2SO_4$ and 4.3 cc. (0.1 mol) of 98.1% $HNO_3$. After 30 minutes of dropwise addition of the acid mixture at a temperature of 0° to 5° C., the mixture was then stirred at 25° C. for an additional hour. The resulting reaction product was extracted with methylene chloride, the extracts treated with silica gel, and the methylene chloride solvent removed to give 14.94 grams (about an 89% yield) of the mononitrated o-xylenes mixture of which about 5%, by weight, thereof was unreacted xylene.

EXAMPLE 6

16.1 grams (0.1 mol) N-methylphthalimide dissolved in 30 cc. 98.3% $H_2SO_4$ and 40 cc. methylene chloride was brought to a slow reflux (about 41° C.) at which point 4.55 cc. (0.105 mol) 98.1% $HNO_3$ was added slowly to the reaction mixture over a period of 40 minutes. Thereafter, the mixture was stirred for an additional 1 hour at 41° C. while allowing some of the methylene chloride to be distilled. Thereafter, the temperature of the reaction mixture was raised to 90° C. for a period of 2 hours at which point the reaction mixture was cooled, diluted with 10 cc. $H_2O$ and the solution extracted with 200 cc. portions of methylene chloride. Evaporation of the methylene chloride solvent yielded 18.6 grams (90% of the theoretical yield) of which 90%, by weight, was a 4-nitro-N-methylphthalimide, 4% was the 3-nitro-N-methylphthalimide and 4% of unreacted N-methylphthalimide.

When N-isopropylphthalimide was reacted in the same way with an equimolar amount of nitric acid, 19.8 grams of product was obtained of which 85% was the 4-nitro-N-isopropylphthalimide, 5% was the 3-nitro-N-isopropylphthalimide, and 7% was recovered starting materials.

EXAMPLE 7

This example illustrates the mononitration of phthalic anhydride at superatmospheric pressure. More particularly, 1.48 grams (0.01 mol) phthalic anhydride and 4 cc. of 100% $H_2SO_4$ were added to a glass pressure reactor (50 cc. volume) fitted with a Teflon valve pressure seal and a magnetic stirring bar. 4 cc. methylene chloride and 0.694 gram (0.011 mol) 98.1% nitric acid were added to the reactor and the valve sealed. The reaction was then stirred vigorously for 2 hours in a water bath held at 75° C. The reaction mixture, which was essentially colorless, was poured into 15 grams of ice and extracted three times with 50 cc. portions of diethyl ether. The extract was passed over a silica gel and evaporated to dryness on a steam bath under nitrogen giving 2.12 grams of light, yellow crystals (theoretical yield 2.11 grams of mononitrophthalic acid). Analysis of both the extracts and the solid showed them to contain 68% of 4-nitrophthalic acid, and 32% of 3-nitrophthalic acid without any evidence of recovered starting materials, indicating that the reaction had gone essentially to completion to the mononitrated derivative. The 100% conversion of the phthalic anhydride to the mononitrated derivative and the lack of color development indicate that this process of superpressure nitration of phthalic anhydride with methylene chloride may offer substantial commercial advantages in making the mononitrophthalic anhydride.

EXAMPLE 8

The following example shows the formation of other mononitro compounds formed from various other aromatic compounds using the procedures of Examples 5 to 7. The following Table II shows the results of such tests whereby only one nitro group was introduced into the aromatic compound, regardless of whether the aromatic compound consisted of a single aromatic nucleus or two aromatic nuclei. All nitrations used 0.1 mol of aromatic compound. Equivalent amounts (0.1 mol) of 98.3% nitric acid were used except for acenaphthene where 70% nitric acid was used. The benzene reaction used a 5% molar excess of nitric acid. The first time tabulated is for the addition of nitric acid; the following times denote heating periods at the corresponding temperatures. All the nitrated materials were readily extracted from the sulfuric acid with methylene chloride using 100 to 300 cc. portions except for the nitroacetanilide which because it was insoluble was extracted with diethyl ether. In each instance from 30 to 50 cc. of methylene chloride was used as solvent during the nitration per 0.1 mol of aromatic compound.

TABLE II

| Compound | H₂SO₄ cc | % Concent. | Temp. (°C) | Time (hr) | Products Total Weight Reaction Product (grams) | % Yield Mononitrated Product |
|---|---|---|---|---|---|---|
| Benzene | 15 | 80 | 41 41 | 0.5 1.5 | 12.11 | 96.5 |
| Toluene | 15 | 80 | 41 41 | 0.5 1.5 | 13.62 | 96.9 |
| Chlorobenzene | 10 | 96.5 | 41 41 | 0.5 4.0 | 15.54 | 96.8 |
| Benzonitrile | 30 | 95.6 | 0–5 0 | 0.75 1.5 | 7.63 | 49.7 |
| Benzaldehyde | 30 | 95.6 | 0–5 0–5 25 | 0.5 2.0 0.5 | 14.68 | 96.1 |

TABLE II -continued

| Compound | H₂SO₄ cc | % Concent. | Temp. (° C) | Time (hr) | Products Total Weight Reaction Product (grams) | % Yield Mononitrated Product |
| --- | --- | --- | --- | --- | --- | --- |
| Benzoic acid | 15 | 95.6 | 41 | 0.5 | 15.36 | 90.5 |
|  |  |  | 41 | 1.5 |  |  |
| Acetanilide | 30 | 95.6 | 0–5 | 0.75 | 15.00 | 80.3 |
|  |  |  | 0 | 2.5 |  |  |
| Naphthalene | 15 | 80 | 41 | 0.75 | 17.17 | 94.1 |
|  |  |  | 41 | 4.5 |  |  |
| o-Nitro-phenol | 15 | 80 | 41 | 0.5 | 18.39 | 94.0 |
|  |  |  | 41 | 1.5 |  |  |
| Acenaphthene | 3.25 | 95.5 | 10 | 0.5 | 17.53 | 40 |
|  |  |  | 15 | 1 |  |  |
|  |  |  | 25 | 1 |  |  |

In addition to the aromatic compounds mentioned above and employed in the foregoing examples for nitration purposes, it will be apparent that other aromatic compounds containing from 6 to 18 carbon atoms may be employed within the scope of this invention, many examples of which have been given above. It will also be apparent to those skilled in the art that in addition to the conditions and temperatures, pressures, proportions and concentrations of ingredients employed in the foregoing examples, variations of these may be employed, all within the scope of the intended invention.

The various dinitro compounds described herein and capable of preparation by means of our process can be converted to either diamino derivatives for use in making polymeric compositions, for instance, through initial reaction with dianhydrides or else they can be converted to diisocyanato compounds which can be used for making resinous compositions by reaction with polyols. The mononitro compounds of the present invention may be treated to reduce the nitro group to the amino group and such aminated derivatives can be used in the preparation of various dyes. In addition, aminated derivatives of aromatic hydrocarbons can be reacted with formaldehyde to form resinous compositions useful in the molding art. Nitrophthalic anhydrides, nitrophthalimides or nitrated derivatives of the N-methylphthalimides can be employed in the preparation of polymers having good heat resistance. Thus, the nitrophthalic anhydrides are first reacted with dialkali metal salts of, for instance, bisphenol-A to form a dianhydride of the formula

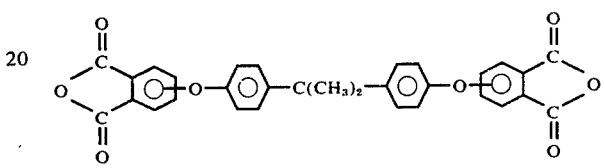

Thereafter this dianhydride can be reacted with organic diamines such as 4,4'-diaminodiphenylmethane, m-phenylene diamine, etc., to give polymers having extremely good high-temperature properties useful as housings for appliances and for motors, as brake linings, etc. The nitro derivatives of N-methylphthalimide can be reacted with bisphenol-A similarly as with the nitrophthalic anhydrides, treated with aqueous sodium hydroxide to form the corresponding tetracarboxylic acid and by suitable treatment of the tetraacid with, for instance, glacial acetic acid and acetic anhydride, one can obtain the corresponding dianhydride having formula I. These again can be used to make polymers by reacting with a diamino compound in the same manner as described previously.

What we claim as new and desire to secure by Letters Patent of the United States is:

1. The process for making 4-nitro-N-methylphthalimide which comprises forming a solution of N-methylphthalimide with methylene chloride and concentrated sulfuric acid having a concentration of at least 90%, treating the said phthalimide solution with concentrated nitric acid of at least 90% concentration at a temperature of from −42° to −45° C., the said nitric acid being close to the stoichiometric amount required to attach one nitro group to the N-methylphthalimide, and thereafter extracting the 4-nitro N-methylphthalimide from the reaction mixture with methylene chloride.

* * * * *

UNITED STATES PATENT AND TRADEMARK OFFICE
CERTIFICATE OF CORRECTION

PATENT NO. : 4,005,102
DATED : *January 25, 1977
INVENTOR(S) : Newell C. Cook; Gary C. Davis It is certified that error appears in the above-identified patent and that said Letters Patent are hereby corrected as shown below:

Column 10, line 49, "-42° to -45°C.," should read

-- 42° to 45°C., --

Signed and Sealed this

Seventeenth Day of July 1984

[SEAL]

Attest:

GERALD J. MOSSINGHOFF

Attesting Officer

Commissioner of Patents and Trademarks